(12) United States Patent
Bell et al.

(10) Patent No.: US 6,193,694 B1
(45) Date of Patent: Feb. 27, 2001

(54) NEEDLE POINT PROTECTION SHEATH

(75) Inventors: David Bell, Grayslake; William J. Schnell, Libertyville, both of IL (US)

(73) Assignee: DSU Medical Corporation, Las Vegas, NV (US)

( * ) Notice: Subject to any disclaimer, the term of this patent is extended or adjusted under 35 U.S.C. 154(b) by 0 days.

(21) Appl. No.: 09/500,567

(22) Filed: Feb. 9, 2000

Related U.S. Application Data

(62) Division of application No. 09/248,654, filed on Feb. 11, 1999, now Pat. No. 6,042,570.

(51) Int. Cl.$^7$ ..................................................... A61M 5/32
(52) U.S. Cl. ...................... 604/192; 604/163; 604/164.08
(58) Field of Search .................................... 604/192, 110, 604/263, 198, 187, 158, 160, 161, 163, 164.08

(56) References Cited

U.S. PATENT DOCUMENTS

| | | |
|---|---|---|
| 4,170,993 | 10/1979 | Alvarez . |
| 4,631,057 | 12/1986 | Mitchell . |
| 4,693,708 | 9/1987 | Wanderer et al. . |
| 4,874,383 | 10/1989 | McNaughton . |
| 4,906,235 | 3/1990 | Roberts . |
| 4,935,012 | 6/1990 | Magre et al. . |
| 4,941,881 | 7/1990 | Masters et al. . |
| 4,950,242 | 8/1990 | Alvarez . |
| 4,985,020 | 1/1991 | Kasuya . |
| 5,120,311 | 6/1992 | Sagstetter et al. . |
| 5,401,250 | 3/1995 | Shields . |
| 5,833,670 | 11/1998 | Dillon et al. . |

*Primary Examiner*—John B. Yasko
(74) *Attorney, Agent, or Firm*—Garrettson Ellis; Seyfarth Shaw

(57) ABSTRACT

A needle point protection sheath comprises a protector tube having a bore for receiving a hollow needle plus a needle hub within the bore. The protector tube has closure cap at one end thereof and has a retention member at the other end to engage an end of the hub, to prevent the hub from passing out of the other tube end. The cap may carry a sleeve having a needle-pierceable wall at its inner end, or a mass of resilient material which is capable of being penetrated by the needle as the cap is closed, to seal the needle tip and thus prevent the spilling of blood residue when a blood collection needle is being enclosed for protection.

10 Claims, 6 Drawing Sheets

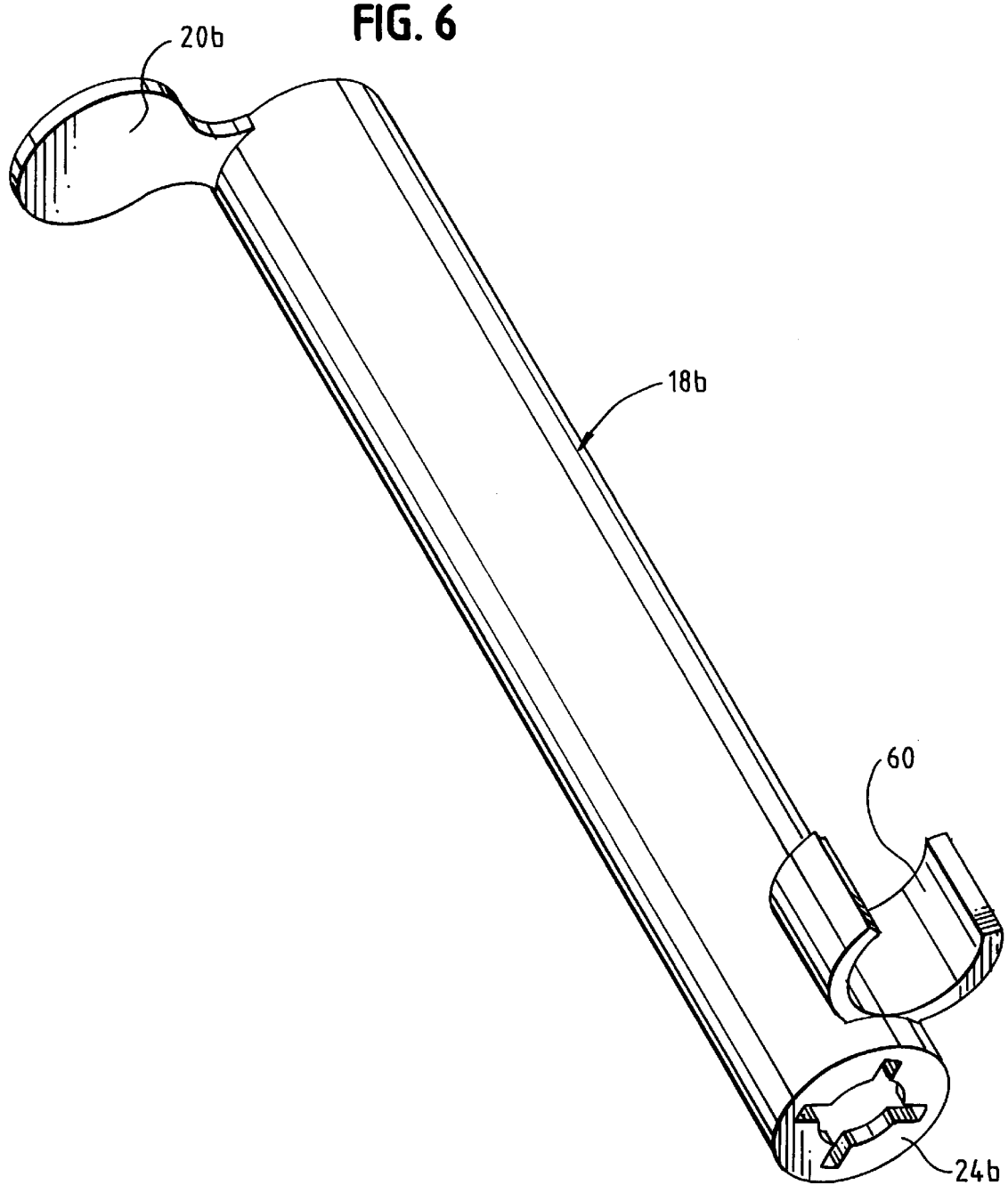

NEEDLE POINT PROTECTION SHEATH

CROSS REFERENCE TO RELATED APPLICATION

This is a division of U.S. application Ser. No. 09/248,654, filed Feb. 11, 1999 now U.S. Pat. No. 6,042,570.

BACKGROUND OF THE INVENTION

A large number of different designs of sheaths and the like for the protection of users against medical needle points is known. After use, a medical needle may represent a substantial biohazard because of the possibility of AIDS or another bacterial or viral disease, which may be transmitted form a carrier to subsequent handlers of the needle by accidental needle stick. For example, various U.S. patents are known pertaining to sheaths for winged needles, such as Utterberg U.S. Pat. Nos. 5,112,311; 5,266,072; 5,290,264; 5,562,637; 5,704,924 and more.

Also, needle protector sheaths for wingless needles are known, such as Alverez U.S. Pat. No. 4,170,993, Magre et al. U.S. Pat. No. 4,935,012, Wanderer et al. U.S. Pat. No. 4,693,708, and Kasuya U.S. Pat. No. 4,985,020, among others.

A common design of needle for a blood collection set carries the needle on the end of a blood collection tube by means of a rubber hub which is shorter than the needle, but transversely enlarged compared with the width of the needle. Also, such a rubber hub is roughly in the form of a rectangular block, but with an irregular surface. The needle is without wings, so the technology of needle sheath designs which are used with winged needles is not usable here. Also, the prior art for shielding of wingless needles has not proven to be practical for the shielding of needle sets of the above described design.

By this invention, a needle tip protector tube can be provided for a medical fluid flow set in which a needle is carried with a transversely enlarged hub having an irregular surface and generally of a length shorter than that of the needle. Preferred embodiments of the protector tube of this invention can provide sealing to the tip of the needle, which is desired when the set carrying the needle is a blood set, to avoid the spilling of blood out of the needle tip. Also, the protector rube is inexpensive, simple, and reliable for use. Particularly, it may be carried on the tubing of the set and then advanced to surround and seal the needle tip when desired, so that one does not have to poke the needle through one end of the protector tube as part of the tube application process. That action has been a source of needle stick accidents.

DESCRIPTION OF THE INVENTION

By this invention, a needle point protection sheath is provided, which comprises a protector tube having a bore for completely receiving a hollow needle with its point positioned within the bore, and also for receiving the needle hub completely within the bore. The protector tube preferably carries a closure cap at one end thereof. At its other end, the protector tube has a retention member to engage an end of the hub, to prevent the hub from passing out of the other tube end.

Thus, the protector tube may be strung upon tubing of the set that carries the needle with the set tubing extending through the bore of the protector tube. When its use is desired, the protector tube may be advanced along the set tubing until the attached hub and needle are enclosed in the protector tube. The retention member prevents the hub from passing out of the protector tube at one end, while at the other end the closure cap may then be closed, so that the tip of the needle is shielded.

The closure cap may carry a sleeve which projects inwardly of the protector tube when the cap is closed. The sleeve is closed at an inner end with a needle pierceable wall, if desired, whereby a tip of a needle carried within the tube can pierce the wall to be enclosed and at least to substantially seal the needle point in the sleeve as the cap is closed.

If desired, the inwardly projecting sleeve may be filled with a needle point sealing mass carried on the closure cap such as rubber, latex, sealant, or the like, to sealingly receive a penetrating needle point of a needle carried in the tube when the cap is closed, to seal the end of the needle and prevent leakage. Alternatively, the sealing mass may be used apart from the inwardly projecting sleeve by simply attaching a self-supporting mass of rubber or other sealant material to the inner surface of the closure cap.

At the other end of the protector tube, the retention member may comprise a flange having an inwardly facing surface which is substantially perpendicular to the axis of the tube, and an outwardly facing surface defining an acute angle to the tube. Thus, a needle hub may be placed into the tube with its surfaces engaging the outwardly facing surface in the acute angle relationship, to spread the tube end and then to snap into a locked position which is created by the substantially perpendicular, inwardly facing surface. This perpendicular surface engages the end of the hub to prevent withdrawal of the same.

Alternatively, the retention member may comprise a plurality of plates attached to an interior surface of the protector tube, or the end thereof, and extending radially inwardly to define a restricted aperture of a size that permits flexible tubing attached to the needle hub to extend through the aperture with essentially no excess space. The plates are angled slightly in the direction of the protector tube longitudinal axis. Thus, the flexible tubing may slide in one direction through the restricted aperture, but is substantially prevented from sliding through the restricted aperture in the direction opposed to the one direction by flexing and gripping of the plates. The plates, while somewhat flexible, are rigid enough to provide this effect, similar in principle of operation in some ways to a Tinnerman washer.

The closure cap is preferably hinged to one end of the protector tube, and carries an attached finger grip, for example a ring. The closure cap preferably has a relatively thick outer wall to form a barrier to the pointed end of a needle enclosed in the interior of the protector tube.

If desired, the protector tube may have a longitudinal slot extending its entire length, to permit application of the needle guard laterally to the flexible tubing.

Preferably, a medical fluid and flow set is provided which comprises a flexible tube having a needle hub at an end thereof, and a hollow needle having a point carried by the hub. The protector tube of this invention may be frustoconical or cylindrical, for example, surrounding at least one of the tube, hub, and needle depending upon its desired position, being slidingly movable along the set. The frustoconical protector tube has respective larger and smaller ends, with the large tube end facing in the same direction as the needle point. The smaller tube end is proportioned to surround and tightly squeeze against the hub, so that the protector tube resists withdrawal rearwardly along the set once it is pushed into a position of engagement with the hub. The protector tube is of a length to enclose the needle point when the smaller tube end encloses and squeezes the hub.

Generally, a closure cap is provided for the larger tube end, preferably a hinged cap.

Also, the protector tube preferably defines a retention member at its smaller end to prevent the hub from passing out of the smaller tube end. Thus, relative motion between the protector tube and the needle and hub can be basically eliminated when the hub is drawn up from a position back along the tubing of the set into engagement with the hub while enclosing the needle. The closure cap is closed, and the needle point is thus reliably enclosed so that subsequent handlers of the set are protected.

The particular design of retention member can be similar to those designs described above. Also, the previously described sleeve carried by an inner surface of the closure cap and projecting inwardly of the tube may be used to seal the needle tip in the manner previously described, as can the previously described needle point sealing mass of rubber or the like.

Thus, a simple needle point protection sheath comprising a protector tube is provided for reliable sealing of needles carried on blood collection and other sets which typically have a relatively enlarged hub relative to the needle and connected tube. The sheath is relatively inexpensive, providing reliable protection and also providing sealing of the point of the needle if desired.

DESCRIPTION OF THE DRAWINGS

In the drawings,

FIG. 6 is a perspective view of another embodiment of the protector tube of this invention.

DESCRIPTION OF SPECIFIC EMBODIMENTS

Figure 1:
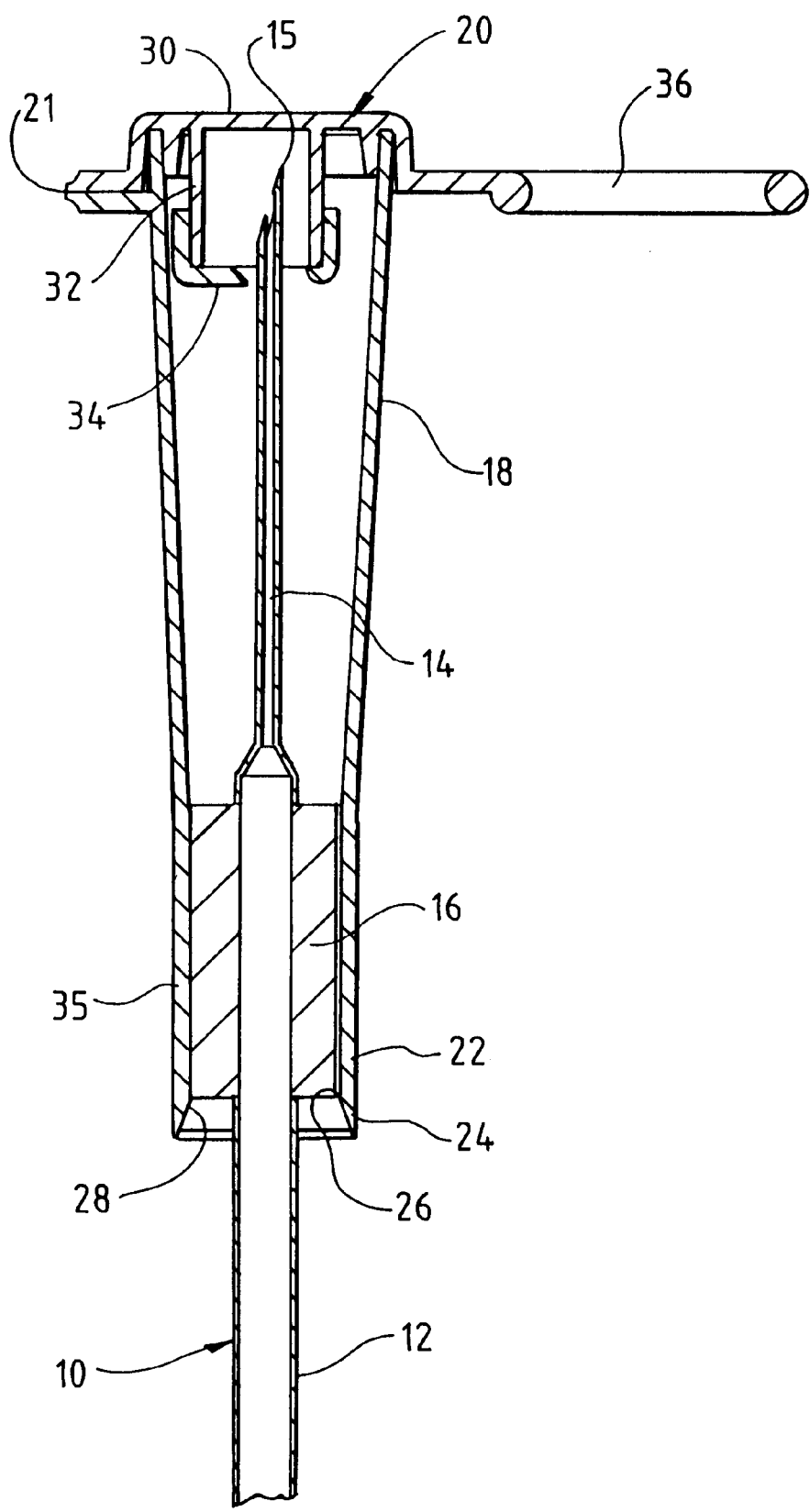
FIG. 1 is an elevational view, taken partly in section, of the front portion of a medical fluid flow set in which a protector tube of this invention is enclosing the needle.
Figure 2:
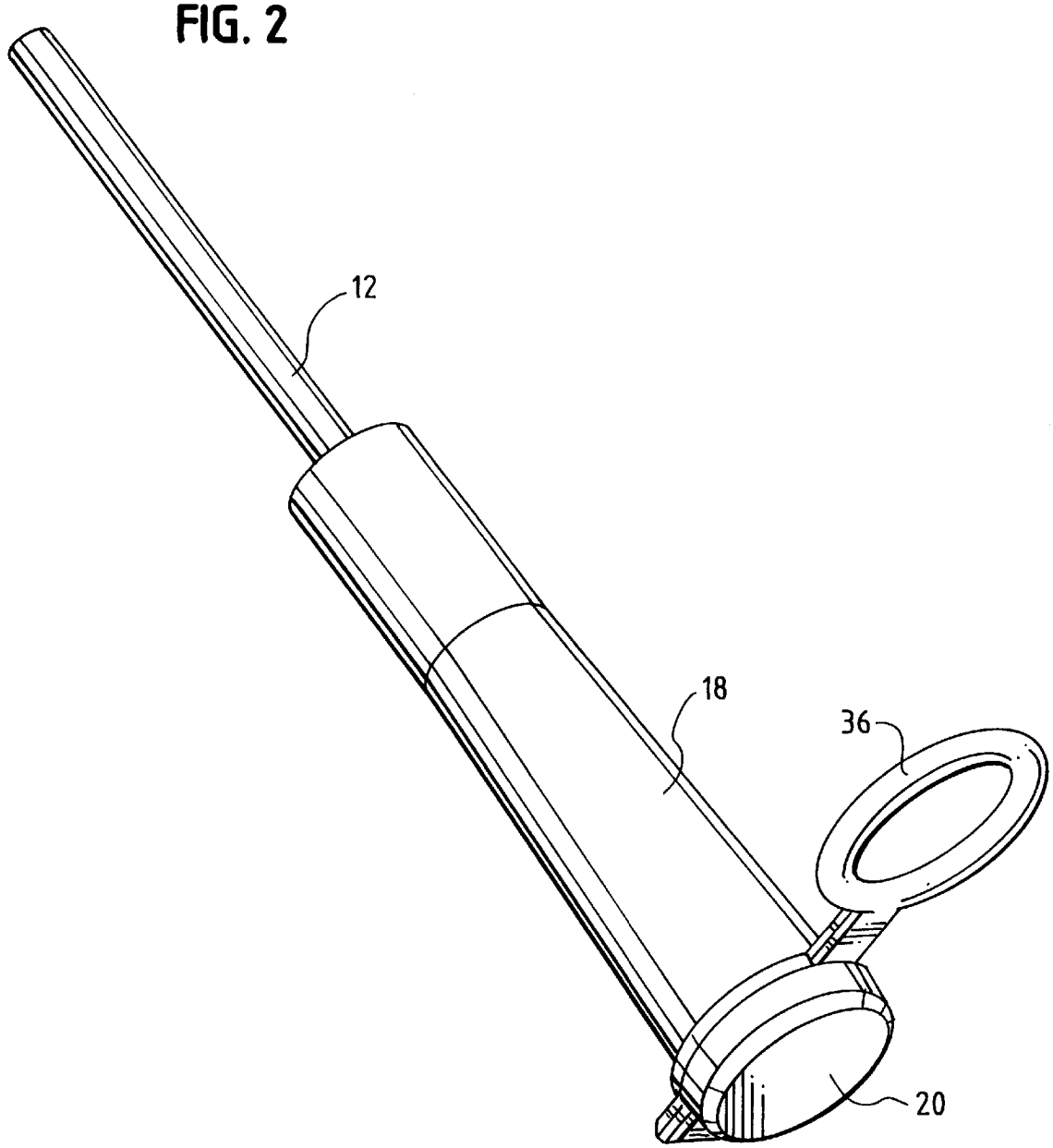
FIG. 2 is a perspective view of the portion of the needle set illustrated in FIG. 1.
Figure 3:
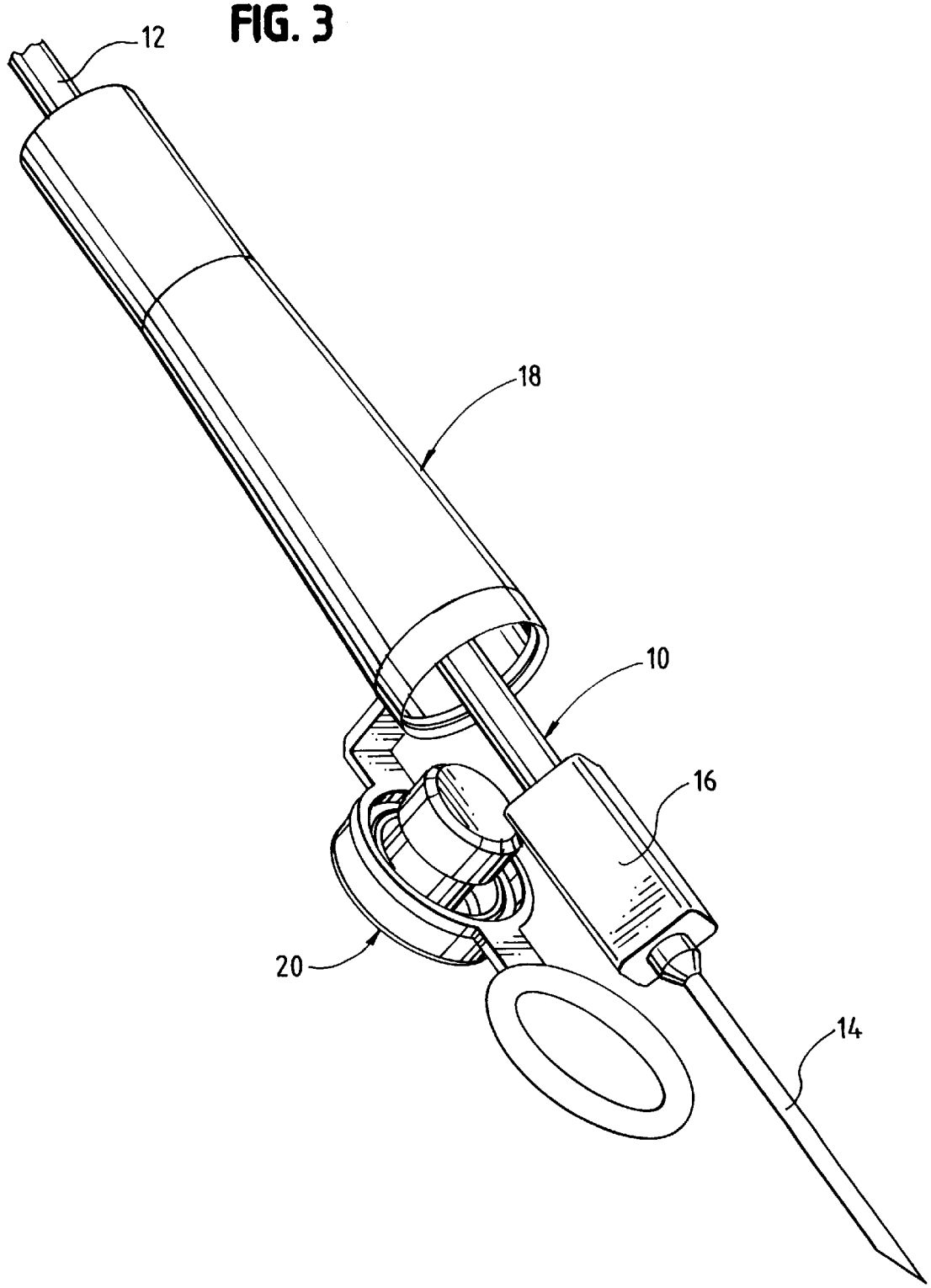
FIG. 3 is a perspective view of the portion of the needle set of FIG. 1, showing how the protector tube may initially be in a retracted position which does not enclose the needle.

Referring to FIGS. 1 through 3, the needle-carrying portion of a conventional blood collection set 10 is shown, with flexible set tubing 12 shown to be connected to a needle 14 via hub 16. Specifically, the design of needle and hub carried on tubing may be of the design used by the blood collection sets of the Fenwal Division of Baxter International, Deerfield, Ill.

In FIG. 1, needle 14 and hub 16 are shown to be surrounded by a protector tube 18, which is shown to be of generally frustoconical shape, and having a cap 20 at its larger, outer end connected by an integral plastic hinge 21.

Smaller protector tube end 22 is shown to be proportioned to surround and squeeze against hub 16, so that protector tube 18 may be retained on the hub, to resist rearward movement relative to the needle and hub 14, 16 as shown in FIG. 1.

Furthermore, protector tube 18, at its smaller, inner end, has an annular retention member 24 which comprises a flange having an inwardly facing surface 26, which surface is perpendicular to the axis of tube 18. Retention member flange 24 also has an outwardly facing, annular surface 28, which defines an acute angle to the tube axis on the order of 30°, as shown. Thus, a needle hub may be placed into the protector tube 18 through the smaller tube end, as when the protector tube is being initially applied to the needle and hub. As needle hub 16 is advanced through the smaller tube end, it engages the acutely angled surfaces 28, and slides into a snap-fit retention relationship between the perpendicular, annular surface 26 and the adjacent end of hub 16. Thus, once inserted, needle hub 16 cannot be withdrawn from the smaller end of protector tube 18.

As shown in FIG. 3, protector tube 18 may initially reside on the blood collection set 10 in a substantially retracted position along tube 12, out of the way of needle 14 as the needle is in use, penetrating into the vein of a patient for blood collection. Cap 20 can be seen to be open in this stage. Then, protector tube 18 may be advanced as needle 14 is withdrawn from the patient into the configuration of FIG. 1, with the engagement between the adjacent end of hub 16 and annular, perpendicular surface 26 preventing the hub from withdrawing out of the small end of protector tube 18. Then, cap 20 may be closed to enclose and seal the needle. Wall 30 of cap 20 may be of a material sufficiently thick that it strongly resists penetration by the point of the needle.

As a further optional feature, closure cap 20 may carry a sleeve 32 projecting inwardly of protector tube 18 when cap 20 is closed on the tube larger end. Sleeve 32 may be closed at an inner end with a needle-pierceable wall 34, in the form of a cap secured to sleeve 32. Thus, as cap 20 closes, pivoting about hinge 21, the tip 15 of needle 14 can be pierce the needle-pierceable cap or wall 34 to enclose the needle point in the sleeve in at least substantially sealed manner.

To obtain a better seal if desired, sleeve 32 may be filled with a sealant material, such as elastomer, which needle tip 15 penetrates. Alternatively, sleeve 32 and penetrable wall 34 may be completely replaced by a plug of elastomer material, other sealant, or the like, which is penetrated by needle tip 15 to seal the needle tip when cap 20 is closed and the needle is retained in protector tube 18.

Thus, the needle is reliably encloses so that subsequent handlers of the set are safe from needle stick injury, while the tip of the needle may be sealed so that residual blood in the set does not leak out.

While being of generally frustoconical shape, protector tube 18 may, if desired, have a cylindrical segment 35 adjacent to one or the other ends, particularly its smaller end, as shown in FIG. 1.

Figure 4:
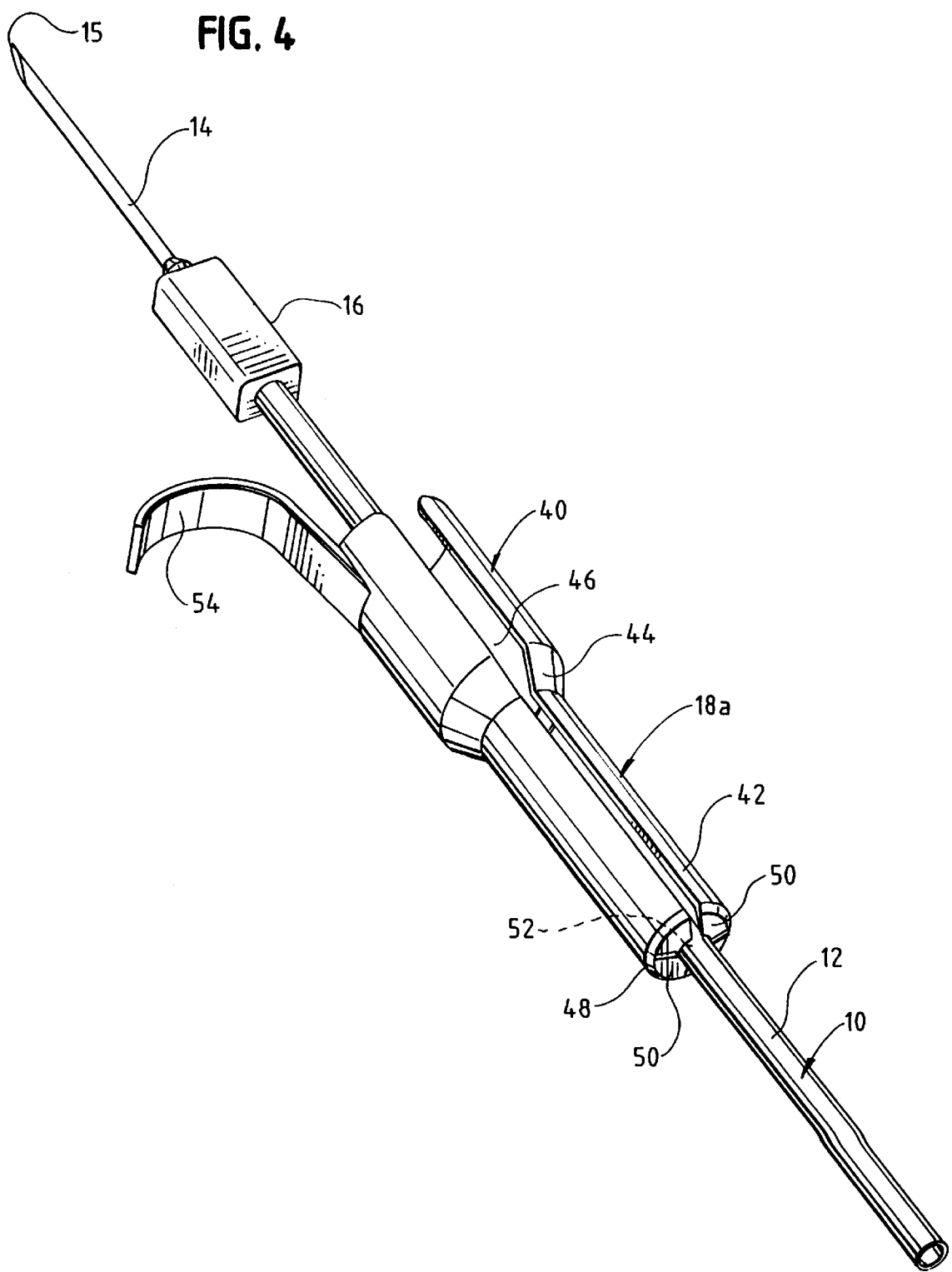
FIG. 4 is a perspective view of a portion of a medical fluid flow set which carries a protector tube of a different embodiment in accordance with this invention.
Figure 5:
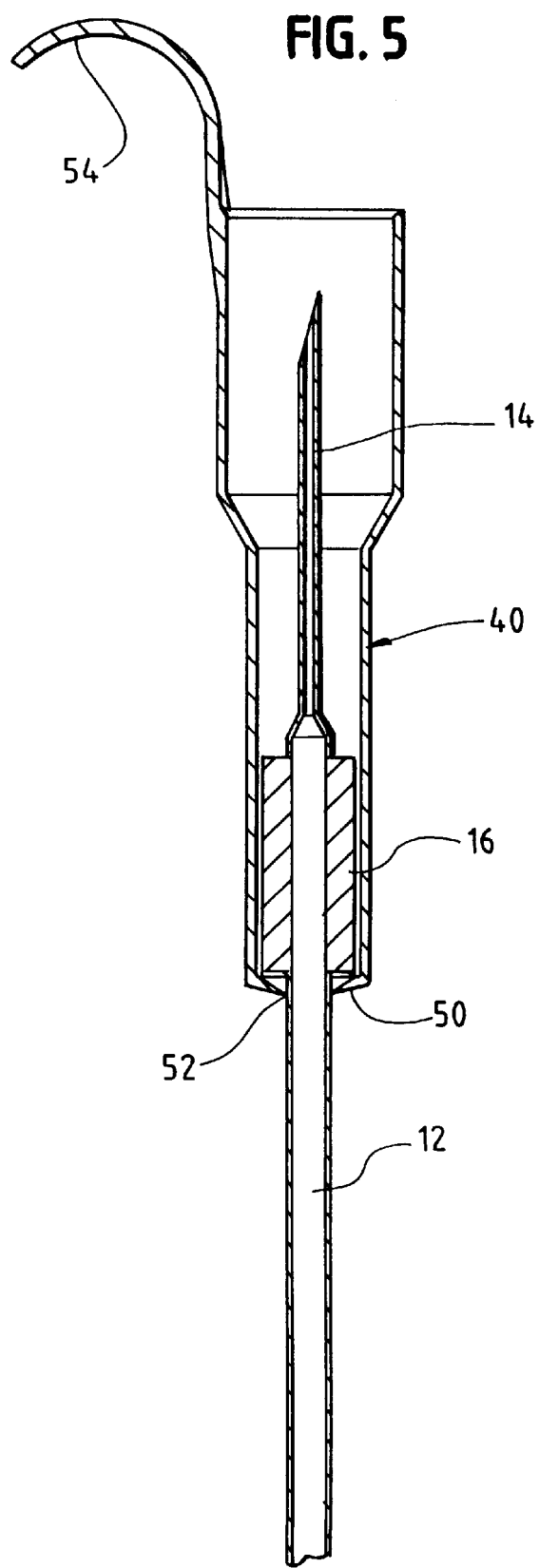
FIG. 5 is an elevational view of the needle set and protector tube of FIG. 4, shown in longitudinal section.

Referring to FIGS. 4 and 5, the same blood collection set 10 comprising flexible tubing 12, needle 14, and rubber hub 16 is shown to carry another embodiment of the plastic protector tube 18a of this invention. The protector tube is shown to comprise a pair of connected cylindrical sections 40, 42 connected with a frustoconical section 44. Protector tube 40 also carries a longitudinal slot 46 extending from end to end of the tube, to permit the protector tube 40 to be laterally placed upon a blood collection set after manufacture when that is desired, when the smaller end 48 of protector tube 40 is too small to allow hub 26 to pass through in either direction.

As shown, protector tube 40 has a retention member comprising a plurality of plates 50 attached at smaller end 48 of protector tube 40. Plates 50 extend radially inwardly to define a restricted aperture 52 of a size that permits flexible tubing 12 to extend through the aperture with substantially no excess space. Plates 50 are angled slightly in the direction of the protector tube longitudinal axis, facing away from needle point 15. Thus, flexible tubing 12 may slide rearwardly; i.e., protector tube 40 may be advanced toward needle 14 with the retention member plates 50 permitting such sliding. However, when one attempts to again retract protector tube 40 by sliding it away from needle 14, plates 50 are forced toward a more perpendicular position with respect to the axis of protector tube 40, digging into flexible tube 12 and preventing such sliding motion of tube 12. Thus, one may completely advance protector tube 40 so that needle 14 is enclosed within the protector tube. Then, it becomes effectively impossible to pull needle 14 out again from its enclosed position within protector tube 40. Needle 14 cannot tip sideways to project out of slot 46, since the hub 16 may be firmly trapped and immobilized within smaller tubing section 42. If desired, a cap may be provided in accordance with preceding embodiments of FIGS. 1–3.

Also, a finger grip 54 may be provided to protector tube 40.

FIG. 5 shows protector tube 40 in its advanced position, providing further illustration how the plates 50 of the retention member prevent a subsequent advancement of needle 14 out of protector tube 40 after the position of FIG. 5 has been achieved.

Referring to FIG. 6, another embodiment of protector tube 18*b* is disclosed. Protector tube 18*b* comprises a cylindrical tube having a retention member 24*b* comprising a radial flange at its proximal end and a hinged cap 20*b* at its distal end. This design may be applied to blood collection sets during manufacture, before application of the hub and needle, by stringing it onto the tubing from which the set is to be made. A retention clip 60 may be provided to receive tubing which is folded over and placed into clip 60, after the needle of the set has been used, and after protector tube 18*b* is advanced to enclose the needle and hub, so that the engagement of set tubing with retention clip 60 may serve as a lock for protector tube 18*b*.

The above has been offered for illustrative purposes only, and is not intended to limit the scope of this application, which is defined in the claims below.

That which is claimed:

1. A medical fluid flow set which comprises a flexible tube having a needle hub at an end thereof, said hub carrying a hollow needle having a point, and being of enlarged transverse dimension relative to said needle; a protector tube surrounding at least one of said tube, hub, and needle, said tube being of a length to enclose said needle, said tube defining a retention member at one end to prevent said hub from passing out of said one end, said retention member comprising a plurality of plates attached to an interior surface of said protector tube and extending radially inwardly to define a restricted aperture of a size that permits flexible tubing attached to said needle hub to extend through said aperture, said plates being angled slightly from a direction perpendicular to the protector tube longitudinal axis, whereby said flexible tubing may slide in one direction through the restricted aperture, but is substantially prevented from sliding through the restricted aperture in the direction opposed to said one direction by flexing and gripping of said plates.

2. The flow set of claim 1 in which a closure cap is provided at one protector tube end.

3. The flow set of claim 1 in which said closure cap carries a sleeve projecting inwardly of said tube when the cap is closed, said sleeve being closed at an inner end with a needle pierceable wall, whereby a tip of a needle carried within the tube can pierce said wall to enclose and at least substantially seal the needle point in the sleeve.

4. A needle point protection sheath which comprises a protector tube having a bore for receiving a hollow needle having a point within said bore and a needle hub, said protector tube having a retention member at a first end thereof to engage an end of the hub to prevent said hub from passing out of the other tube end, said retention member comprising a plurality of plates attached to an interior surface or end of said protector tube and extending radially inwardly to define a restricted aperture of a size that permits flexible tubing attached to said needle hub to extend through said aperture, said plates being angled slightly in the direction of the protector tube longitudinal axis, whereby said flexible tubing may slide in one direction through the restricted aperture, but is substantially prevented from sliding through the restricted aperture in the direction opposed to said one direction by flexing and gripping of said plates.

5. The protection sheath of claim 4 which has a closure cap at a second end thereof, said closure cap carrying a sleeve projecting inwardly of said tube when the cap is closed, said sleeve being closed at an inner end with a needle-pierceable wall, whereby a tip of a needle carried within said tube can pierce said wall to enclose and at least substantially seal the needle point in the sleeve.

6. The protection sheath of claim 5 in which a needle point sealing mass is carried on said closure cap to sealingly receive a penetrating needle point of a needle carried in said tube when the cap is closed, to seal the end of said needle.

7. The protection sheath of claim 6 in which said needle point sealing mass comprises rubber.

8. The protection sheath of claim 4 which has a closure cap at a second end thereof.

9. A needle guard carried with a set comprising a medical needle mounted on flexible tubing, said needle having a hub, said guard comprising a protector tube open at both ends with said flexible tubing extending completely through said protector tube, said protector tube having an interior large enough to receive and enclose said needle and said hub, one end of said protector tube having a retention member for engaging an end of said hub to substantially prevent withdrawal of said needle and hub from the protector tube interior through said one end, said protector tube having a longitudinal slot extending its entire length to permit application of said needle guard laterally to said flexible tubing.

10. The needle guard and set of claim 9 in which said retention member comprises a plurality of plates attached to an interior or end surface of said protector tube and extending radially inwardly to define a restricted aperture of a size that permits said flexible tubing to extend through said aperture with essentially no access space, said plates being angled slightly in the direction of the protector tube longitudinal axis, whereby said flexible tubing may slide in one direction through the restricted aperture, but is substantially prevented from sliding through the restricted aperture in a direction opposed to said one direction by flexing and gripping of said plates.

* * * * *